United States Patent [19]

Causse et al.

[11] Patent Number: 5,723,109
[45] Date of Patent: Mar. 3, 1998

[54] USE OF SALICYCLIC ACID DERIVATIVES FOR DEPIGMENTING THE SKIN

[75] Inventors: Catherine Causse, Paris; Sabine Deprez, Thiais, both of France

[73] Assignee: L'Oreal, Paris, France

[21] Appl. No.: 627,965

[22] Filed: Apr. 4, 1996

[30] Foreign Application Priority Data

Apr. 7, 1995 [FR] France ................... 95 04189

[51] Int. Cl.$^6$ ................................. A61K 7/48
[52] U.S. Cl. ................ 424/62; 424/401; 424/450; 424/489; 514/159; 514/844; 514/846; 514/938; 514/944
[58] Field of Search ................ 424/62, 401, 450, 424/489, 159; 514/844, 846, 938, 944

[56] References Cited

U.S. PATENT DOCUMENTS

| | | | |
|---|---|---|---|
| 5,164,185 | 11/1992 | Charpin et al. | 424/401 |
| 5,262,407 | 11/1993 | Leveque et al. | 514/159 |

FOREIGN PATENT DOCUMENTS

| | | |
|---|---|---|
| 0 378 936 | 7/1990 | European Pat. Off. . |
| 0 570 230 | 11/1993 | European Pat. Off. . |
| 0 662 318 | 7/1995 | European Pat. Off. . |
| 0 680 748 | 11/1995 | European Pat. Off. . |
| WO 91/05543 | 5/1991 | WIPO . |

*Primary Examiner*—Jyothsan Venkat
*Attorney, Agent, or Firm*—Oblon, Spivak, McClelland, Maier & Neustadt, P.C.

[57] ABSTRACT

Salicylic acid derivatives act as inhibitors of tyrosinase and are used in compositions for the purpose of lightening the skin or of treating pigmental blemishes.

15 Claims, 1 Drawing Sheet

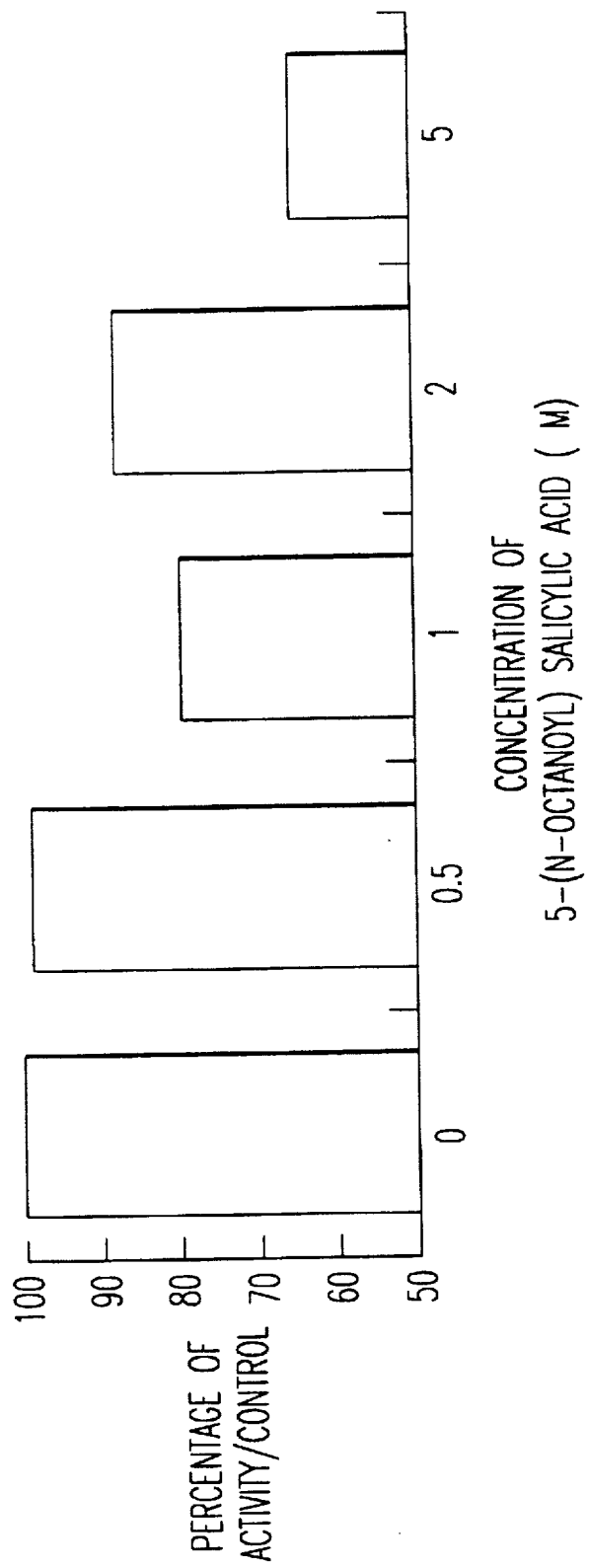

USE OF SALICYCLIC ACID DERIVATIVES FOR DEPIGMENTING THE SKIN

BACKGROUND OF THE INVENTION

1. Field of the Invention

The invention relates to the use of salicylic acid derivatives in or for the preparation of a cosmetic or dermatological composition for topical application to the skin of the face and/or of the body, for the purpose of lightening the skin or of treating pigmental blemishes without desquamation or peeling of the skin.

2. Discussion of the Background

At different periods in their life, some people witness the appearance on the skin and more especially on the hands of darker and/or more highly colored blemishes which give the skin a heterogeneous appearance. These blemishes are due to a high concentration of melanin in the keratinocytes situated at the surface of the skin. In fact, melanocytes situated in the underlying part of the epidermis produce melanin and deliver this melanin to the surrounding keratinocytes which, laden with melanin, will then rise to the surface of the epidermis.

The mechanism of formation of skin pigmentation, that is to say of the formation of melanin, is particularly complex and involves, schematically, the following main stages:

Tyrosine→Dopa→Dopaquinone→Dopachrome→Melanin

Tyrosinase is an essential enzyme which takes part in this sequence of reactions. It catalyses in particular the conversion reaction of tyrosine to Dopa (dihydroxyphenylalanine) and the conversion reaction of Dopa to dopaquinone. The tyrosinase only acts when it is in the maturation state under the effect of certain biological factors.

A substance is recognized as depigmenting if it acts directly on the vitality of the epidermal melanocytes where melanogenesis takes place and/or if it interferes with one of the stages in the biosynthesis of melanin, either by inhibiting one of the enzymes involved in melanogenesis or by being inserted as a structural analogue of one of the chemical compounds in the sequence for the synthesis of melanin, which sequence can thus be blocked and ensure depigmentation.

The substances most commonly used as depigmenting agents are more particularly hydroquinone and its derivatives, in particular its ethers, such as hydroquinone monomethyl ether and monoethyl ether. These compounds, although they are certain to be effective, are unfortunately not free of side effects due to the toxicity which they bring about, which can make their use problematic or indeed dangerous. This toxicity arises from their intervention in fundamental mechanisms of melanogenesis, killing cells which then risk disturbing their biological environment and which consequently oblige the skin to discharge them, producing toxins.

Thus, hydroquinone, the use of which is moreover legally restricted to a concentration of 2%, is a compound which is particularly irritating and cytotoxic for melanocytes, the complete or partial replacement of which has been envisaged by many writers.

The use of inoffensive topical depigmenting substances which are highly effective is very particularly sought after with a view to treating regional hyperpigmentations by melanocytic hyperactivity such as idiopathic melasmas, arising during pregnancy ("mask of pregnancy" or chloasma) or estrone/progestogen contraception, localized hyperpigmentations by benign melanocytic hyperactivity and proliferation such as senile pigmental blemishes known as actinic lentigines, accidental hyperpigmentations such as photosensitization and post-lesional scarring, as well as certain leucodermas such as vitiligo. For the latter hyperpigmentations, for want of being able to repigment the damaged skin, the end result is to depigment the remaining normal skin regions to give the whole skin a homogeneous white coloring.

A search has thus been carried out for substances which do not interfere in the mechanism of melanogenesis but which act upstream on tyrosinase, preventing its activation, and which are, for this reason, much less toxic. Kojic acid is commonly used as an inhibitor of the activation of tyrosinase. Moreover, U.S. Pat. No. 5,262,153 teaches the use of lactic acid and its derivatives.

Applicants have unexpectedly found that certain salicylic acid derivatives exhibited the property of inhibiting the activation of tyrosinase, and thus its activity, and of thus acting on pigmentation and blemishes of the skin without toxicity.

Certainly, it is known from the document EP-A-378,936 (corresponding to U.S. Pat. No. 5,262,407) to use these salicylic acid derivatives as keratolytic agents for preventing ageing of the skin and, inter alia, for treating pigmented blemishes of senile origin. These keratolytic agents are exfoliants or peeling agents and reduce pigmental blemishes by removing dead cells at the surface of the skin and particularly cells of these blemishes. This document in no way teaches that these salicylic acid derivatives can inhibit the activity of tyrosinase by having melanocytes for target cells and can thus make it possible to reduce the production of melanin.

It has now been observed, surprisingly, that when salicylic acid derivatives are used in low concentration, these compounds have an inhibitory effect on the activity of tyrosinase and depigmented the skin without desquamating it, by acting on the synthesis of melanin and not by removing dead cells. These two action processes, synthesis of melanin and desquamation, are quite different and even conflicting.

Indeed, when a compound desquamates the skin, it creates surface inflammation of the skin, leading to the stimulation of melanin. Consequently, the desquamation leads to a removal of the surface marks from the skin and not to an inhibition of the production of melanin. Thus, when used at concentrations of greater than 3%, the compounds described in document EP-A-378,936 remove marks from the skin by desquamation. There was no reason to suppose that at low concentration these same compounds could slow down or limit melanin synthesis and thereby have, on the contrary, an anti-inflammatory effect. Depending on the concentrations used, these compounds have surprisingly contrasting effects on the skin.

Moreover, document EP-A-570,230 describes the use of alkylated and alkoxylated derivatives of salicylic acid which are at high concentration or in combination with other depigmenting agents, for treating dyschromia. However, it does not teach that other salicylic acid derivatives used alone can have such a property at much lower concentrations. Moreover, compounds even of similar formula may have quite different properties.

SUMMARY OF THE INVENTION

Accordingly, one object of the present invention is to provide a method of inhibiting tyrosinase and a cosmetic or dermatological composition which contains a tyrosinase inhibitor for use in depigmenting the skin without desquamation or peeling of the skin.

This and other objects which will become apparent in the course of the following description have been achieved by the method and composition of the present invention. The method and composition of the invention utilize a salicylic acid derivative of formula (I) or a salt thereof as the only tyrosinase inhibitor:

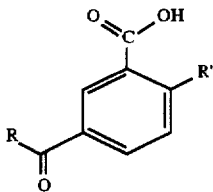
(I)

in which:

R is a linear, branched or cyclic saturated aliphatic group or an unsaturated group containing one or a number of double bonds, which may or may not be conjugated, these groups containing from 2 to 22 carbon atoms and being able to be substituted by at least one substituent selected from (a) halogen atoms, (b) the trifluoromethyl group or (c) hydroxyl groups in the free form or esterified by an acid having from 1 to 6 carbon atoms or else by (d) a carboxyl functional group which is free or esterified by a lower alcohol having from 1 to 6 carbon atoms;

R' is a hydroxyl group or an ester functional group of formula:

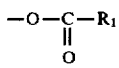

where $R_1$ is a saturated or unsaturated aliphatic group having from 1 to 18 carbon atoms.

The R radical preferably contains at least 4 carbon atoms. It is, for example, formed from a saturated linear alkyl group having from 4 to 11 carbon atoms.

The composition containing a salicylic acid derivative as the only tyrosinase inhibitor according to the invention makes it possible to obtain a marked decrease in, indeed complete disappearance of, the formation of blemishes by inhibiting tyrosinase and also allows one to obtain an inhibition of the biosynthesis of melanin. This effect is obtained by contacting tyrosinase or melanocytes with the salicylic acid derivatives of the invention, for example by contacting pigmented skin with the compounds of the invention. The effect of the invention is obtained when the salicylic acid compounds of the invention are administered to any melanin pigmented skin portion.

BRIEF DESCRIPTION OF THE DRAWING

FIG. 1 shows the inhibitory effect of a salicylic acid derivative of the invention on tyrosinase by evaluating the effect of the derivative on the dopa-oxidase activity of tyrosinase from human melanocytes.

DETAILED DESCRIPTION OF THE PREFERRED EMBODIMENTS

The subject of the present invention is a composition and also the use of an effective amount of a sole inhibitor for inhibiting tyrosinase and the biosynthesis of melanin, in and/or for the preparation of a cosmetic and/or dermatological composition, the inhibitor being a salicylic acid derivative of formula (I) or of a salt of such a derivative:

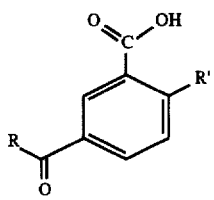
(I)

in which:

R is a linear, branched or cyclic saturated aliphatic group or an unsaturated group carrying one or a number of double bonds, preferably 1–4 double bonds, which may or may not be conjugated, these groups containing from 2 to 22 carbon atoms and being able to be substituted by at least one substituent selected from (a) halogen atoms, (b) the trifluoromethyl group or (c) hydroxyl groups in the free form or esterified by an acid having from 1 to 6 carbon atoms or else by (d) a carboxyl functional group which is free or esterified by a lower alcohol having from 1 to 6 carbon atoms;

R' is a hydroxyl group or an ester functional group of formula:

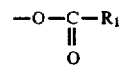

where $R_1$ is a saturated or unsaturated aliphatic group having from 1 to 18 carbon atoms.

These compounds, used in a low amount, have the advantages of depigmenting and lightening skin without peeling it and therefore without irritating it, which is quite surprising for this type of compound.

The salicylic acid derivative is preferably chosen from 5-(n-octanoyl)salicylic, 5-(n-decanoyl)salicylic, and 5-(n-dodecanoyl)salicylic.

The invention also includes salts of these acids, and in particular, the salts obtained by salification with a base. Mention may be made, as base capable of salifying the salicylic acid derivatives according to the invention, of inorganic bases, such as alkali metal hydroxides (sodium and potassium hydroxides) or ammonium hydroxides, or better still organic bases.

Use is preferably made of amphoteric bases for the salification of the salicylic acid derivatives, that is to say bases having both anionic and cationic functional groups. The amphoteric bases can be primary, secondary, tertiary or cyclic organic amines and more especially amino acids. Mention may be made, as examples of amphoteric bases, of glycine, lysine, arginine, taurine, histidine, alanine, valine, cysteine, trihydroxymethylaminomethane (TRISTA) or triethanolamine. These bases are used in amounts which are sufficient to bring the pH of an emulsion of the inventive composition to between 5 and 7 and thus close to that of the skin. It follows that the emulsion of the invention is highly compatible with respect to the skin.

The salicylic acid derivatives or their salts are used, according to the present invention, in an amount preferably ranging from 0.01 to 2% by weight and more preferentially still from 0.2 to 0.5%, relative to the weight of the total composition.

The compositions containing the salicylic acid derivatives according to the invention can have all the pharmaceutical dosage forms normally used for a topical application, for example in the form of aqueous, aqueous/alcoholic or oily solutions, of dispersions of lotion or serum type, of aqueous, anhydrous or oily gels, of emulsions with a liquid or semi-liquid consistency of a milk type, obtained by dispersion of a fatty phase in an aqueous phase (O/W) or vice versa (W/O), or of suspensions or emulsions with a soft, semi-solid or solid consistency of the cream or gel type, or alternatively of microemulsions, of microcapsules, of microparticles or of vesicular dispersions of ionic and/or nonionic type. These compositions are prepared according to conventional methods well known in this art.

The cosmetic or dermatological compositions of the invention can contain, in a known way, adjuvants which are usual in the cosmetic or dermatological field, such as emulsifiers, hydrophilic or lipophilic gelling agents, hydrophilic or lipophilic active principles, preservatives, antioxidants, fragrances, fillers, screening agents and coloring materials. The amounts of these different adjuvants are those conventionally used in the cosmetic and/or dermatological fields and range, for example, from 0.01% to 20% of the total weight of the composition. These adjuvants, depending on their nature, can be introduced into the fatty phase, into the aqueous phase and/or into the lipid vesicles.

Water-in-oil (W/O) or oil-in-water (O/W) emulsifiers can be used as emulsifiers according to the desired final emulsion.

Mention may be made, as emulsifiers, of, for example, PEG-20 stearate, PEG-100 stearate, Polysorbate 60 (TWEEN 60, sold by the company ICI), sorbitan stearate (SPAN 60, sold by the company ICI) and PPG-3 myristyl ether.

The level of emulsifier can range from 0.1% to 15% by weight, and preferably from 0.5% to 5% by weight, with respect to the total weight of the composition.

Coemulsifiers can be added to the composition according to the invention, for example in an amount ranging from 0.05% to 10% by weight with respect to the total weight of the composition. Glyceryl stearate may be mentioned as coemulsifier.

In the lipid vesicle dispersions, the emulsifier can be composed of ionic and/or nonionic lipid vesicles.

Suitable oils which can be used in the invention include inorganic oils, vegetable oils (sunflower oil, apricot kernel oil or karite oil), synthetic oils, silicone oils (cyclomethicone) and fluorinated oils (perfluoropolyethers). Fatty alcohols (stearyl alcohol), fatty acids (stearic acid) and waxes can be added to these oils.

Suitable hydrophilic gelling agents include carboxyvinyl polymers, poly(glyceryl acrylate)s or poly(glyceryl methacrylate)s, polyacrylamides, natural gums (xanthan) and clays and mention may be made, as lipophilic gelling agents, of modified clays, such as bentones, metal salts of fatty acids, such as aluminum stearates, and hydrophobic silica.

Use may be made, as hydrophilic active principles of, for example, proteins or protein hydrolysates, amino acids, polyols, in particular glycerol or sorbitol, urea, allantoin, sugars and their derivatives, or glycyrrhetinic acid.

Suitable lipophilic active principles include tocopherol (vitamin E) and its derivatives, essential fatty acids, ceramides and essential oils.

Use may also be made in these compositions of UV screening agents with lipophilic or hydrophilic properties or titanium and zinc oxides, optionally in the nano-oxide form, in particular for the purpose of obtaining compositions which also ensure good protection against UV radiation.

These compositions constitute in particular protective creams for treating or for caring for the face, for the hands or for the body, protective or care body milks, lotions, gels or foams for caring for or treating the skin, cleansing or disinfecting lotions, bath compositions, foundations and colored creams. In the latter cases, the composition contains pigments.

Other features of the invention will become apparent in the course of the following descriptions of exemplary embodiments which are given for illustration of the invention and are not intended to be limiting thereof.

EXAMPLES

Test:

A test has demonstrated the activity of 5-(n-octanoyl) salicylic acid as an inhibitor of tyrosinase by evaluation of its effect on the dopa-oxidase activity of tyrosinase from human melanocytes.

Human melanocytes were prepared and cultured and then introduced into media containing different concentrations of 5-(n-octanoyl)salicylic acid (0.5 µM, 1 µM, 2 µM and 5 µM).

After three days, the melanocytes were "trypsinizated" in a 0.05%/0.02% trypsin/EDTA mixture in a phosphate buffer (50 mM at pH 6.8), washed three times in phosphate buffer containing 1% (w/v) of TRITON X-100 and subjected to ultrasound. After centrifuging, samples were withdrawn and mixed with 5 mM L-DOPA in phosphate buffer. The tyrosinase activity was evaluated by spectrophotometry. The increase in the absorbance at 475 nm is due to the formation of dopachrome from 5 mM DOPA being measured. The absorbance was read on a microplate reader at 25° C. for 60 min.

The activity of the cellular tyrosinase was measured with respect to a calibration range prepared with commercially available tyrosinase.

The results are presented in FIG. 1 which gives, on the abscissa, the concentrations of 5-(n-octanoyl)salicylic acid, expressed as µM, as a function of the percentage of activity with respect to the starting activity, on the ordinate. These histograms show that the dopa-oxidase activity of the tyrosinase from the melanocytes treated with 5-(n-octanoyl) salicylic acid significantly decreases, which decrease is more particularly pronounced at the concentration of 5 µM.

These results therefore show that 5-(n-octanoyl)salicylic acid modifies cellular melanogenesis by inhibiting the dopaoxidase activity of tyrosinase, that is to say the conversion of L-DOPA to dopaquinone.

The following examples illustrate the invention. In these examples, the proportions shown are percentages by weight.

Example 1

O/W Emulsion

| | |
|---|---|
| 5-(n-Octanoyl)salicylic acid | 1% |
| Octyldodecanol | 5% |
| Sunflower oil | 11% |
| EDTA | 0.05% |
| Sodium hydroxide | 0.02% |
| Xanthan gum | 0.2% |
| Polyacrylamide/Isoparaffin/Laureth-7 (SEPIGEL 305, sold by the company Seppic) | 0.9% |
| Cyclomethicone | 5% |
| Glycerol | 4% |
| Poly(glyceryl acrylate), at 2% in a water/glycerol mixture (LUBRAJEL, sold by the company Guardian) | 5% |
| Glyceryl stearate | 0.6% |
| PEG-100 stearate | 0.6% |
| PEG-20 stearate | 1.2% |
| Stearic acid | 0.6% |
| Stearyl alcohol | 1% |
| Preservatives | 0.3% |
| Water | q.s. for 100% |

A white-colored fluid cream possessing depigmenting properties was obtained.

A test on a panel of 20 women showed that this cream was easy to apply, penetrates well and has a pleasant texture.

Moreover, this cream was the subject of a cosmetoclinical test on 22 women aged from 39 to 65 years with blemishes on the hands and face.

The cream was applied to the face and to the back of the hand for 4 weeks (28 days) at the rate of one application every evening. The women continued to follow their normal personal hygiene and make-up routines.

The attenuation of the blemishes was evaluated by a chromameter before the beginning of the treatment ($D_0$) and after the treatment ($D_{29}$): the coloring of a blemish located on the hand was measured using a CR200 chromameter (Minolta). Measurements were carried out in parallel on the adjacent site of healthy skin serving as a control region. The measurements were carried out three times in the L* and b* system, defining the color space of the skin:

L* defining the luminosity b* defining the color of the skin in the green-blue axis.

From these measurements, the ITA (Individual Typological Angle) was calculated in degrees (°), making it possible to classify skin colors by categories, according to the formula: ITA° angle=[Arctan ((L*-50)/b*)]×180/3.1416.

The significance of the differences between the ITA° angle values taken on the control region and on the pigmented region at $D_0$ and $D_{29}$ was evaluated by the Student test on paired series, giving the value of "t".

The inhibiting effect on tyrosinase of the cream was assessed by its ability to soften the color of the blemish and to give it a color comparable to that of the adjacent healthy skin.

|  | $D_0$ | $D_{29}$ | $D_{29} - D_0$ | 't" | result | significance level |
|---|---|---|---|---|---|---|
| Blemish | 21.20 | 26.65 | 5.45 | 4.459 | *** | 0.1% |
| Control | 43.56 | 45.58 | 2.02 | 1.745 | ns | 10% |
| Control − blemish | 22.36 | 18.34 | 3.43 | 3.816 | ** | 1% |

The results are significant when the significance level is less than 5%. Moreover, the very significant result is recorded: "*" the significant result is recorded: "" and the not significant result is recorded: "ns".

This table shows that the $D_{29}-D_0$ values are very significant and significant for the blemish and the (control-blemish) difference and not significant for the control. These results demonstrate that the application of the cream has clearly softened the blemishes and decreased the difference in coloration between the control region and the blemished region.

Example 2

O/W Emulsion

| | |
|---|---|
| 5-(n-Octanoyl)salicylic acid | 0.5% |
| Apricot kernel oil | 10% |
| Karite oil | 7% |
| PPG-3 myristyl ether | 5% |
| Polysorbate 60 (TWEEN 60) | 2.5% |
| Sorbitan stearate (SPAN 60) | 2.5% |
| Preservatives | 0.2% |
| Cyclomethicone | 4% |
| Xanthan gum | 0.2% |

-continued

| | |
|---|---|
| Carboxyvinyl polymer | 0.5% |
| Triethanolamine (neutralizer) | 0.5% |
| Glycerol | 5% |
| Water | q.s. for 100% |

A good depigmenting day cream was obtained.

Example 3

O/W Emulsion

A composition having depigmenting and screening properties was obtained by adding 2.5% by weight of titanium nano-oxides to the composition of Example 1.

Obviously, numerous modifications and variations of the present invention are possible in light of the above teachings. It is therefore to be understood that within the scope of the appended claims, the invention may be practiced otherwise than as specifically described herein.

French Priority Document 95-04189 filed Apr. 7, 1995 is incorporated herein by reference in its entirety.

What is claimed as new and desired to be secured by Letters Patent of the United States is:

1. A method of lightening skin, comprising contacting skin in need thereof with an effective amount of a salicylic acid compound of formula (I) or of a salt thereof as a sole inhibitor of tyrosinase:

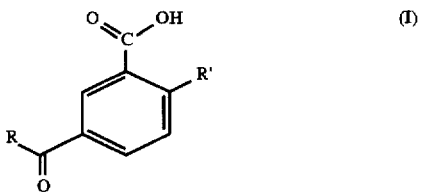

wherein:

R is a $C_{2-22}$ linear or branched or $C_{3-22}$ cyclic saturated aliphatic group or a $C_{2-22}$ unsaturated group containing one or a plurality of double bonds; unsubstituted or substituted by at least one substituent selected from the group consisting of (a) halogen atoms, (b) the trifluoromethyl group, (c) hydroxyl groups in the free form or esterified by an acid having from 1 to 6 carbon atoms and (d) a carboxyl group in the free form or esterified by a lower alcohol having from 1 to 6 carbon atoms;

R' is a hydroxyl group or an ester functional group of the formula:

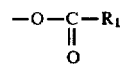

where $R_1$ is a $C_{1-18}$ saturated or unsaturated aliphatic group without peeling the skin.

2. The method of claim 1, wherein said salicylic acid compound is selected from the group consisting of 5-(n-octanoyl)salicylic, 5-(n-decanoyl)salicylic, and 5-(n-dodecanoyl)salicylic acids.

3. The method of claim 1, wherein the salicylic acid compound is 5-(n-octanoyl)salicylic acid.

4. The method of claim 1, wherein the salicylic acid compound is in the form of an inorganic or organic base salt of the salicylic acid compound.

5. The method of claim 1, wherein said salicylic acid compound is present in a cosmetic or dermatologic composition, said composition comprising 0.01–2% by weight of said salicylic acid compound or salt thereof with respect to the total weight of the composition.

6. The method of claim 5, wherein said composition further comprises a UV screening agent.

7. The method of claim 6, wherein said UV screening agent is titanium oxide or zinc oxide.

8. The method of claim 5, wherein said composition is in the form of an aqueous, oily or aqueous/alcoholic solution, a water-in-oil emulsion, an oil-in-water emulsion, a microemulsion, an aqueous gel, an oily gel, an anhydrous gel, a serum or a vesicular dispersion.

9. A method of inhibiting the biosynthesis of melanin, comprising contacting melanin pigmented skin with an effective amount of a cosmetic or dermatologic composition comprising 0.01% to 1% by weight of salicylic acid compound of formula (I) of a salt thereof as a sole inhibitor of tyrosinase:

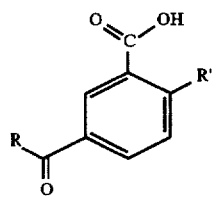

wherein:

R is a $C_{2-22}$ linear or branched or $C_{3-22}$ cyclic saturated aliphatic group or a $C_{2-22}$ unsaturated group containing one or a plurality of double bonds; unsubstituted or substituted by at least one substituent selected from the group consisting of (a) halogen atoms, (b) the trifluoromethyl group, (c) hydroxyl groups in the free form or esterified by an acid having from 1 to 6 carbon atoms and (d) a carboxyl group in the free form or esterified by a lower alcohol having from 1 to 6 carbon atoms;

R' is a hydroxyl group or an ester functional group of the formula:

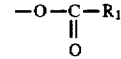

where $R_1$ is a $C_{1-18}$ saturated or unsaturated aliphatic group, without peeling the skin.

10. The method of claim 9, wherein said salicylic acid compound is selected from the group consisting of 5-(n-octanoyl)salicylic, 5-(n-decanoyl)salicylic, and 5-(n-dodecanoyl)salicylic acids.

11. The method of claim 9, wherein the salicylic acid compound is 5-(n-octanoyl)salicylic acid.

12. The method of claim 9, wherein the salicylic acid compound is in the form of an inorganic or organic base salt of the salicylic acid compound.

13. The method of claim 9, wherein said composition further comprises a UV screening agent.

14. The method of claim 13, wherein said UV screening agent is titanium oxide or zinc oxide.

15. The method of claim 9, wherein said composition is in the form of an aqueous, oily or aqueous/alcoholic solution, a water-in-oil emulsion, an oil-in-water emulsion, a microemulsion, an aqueous gel, an oily gel, an anhydrous gel, a serum or a vesicular dispersion.

* * * * *

UNITED STATES PATENT AND TRADEMARK OFFICE
CERTIFICATE OF CORRECTION

PATENT NO.  : 5,723,109
DATED       : March 3, 1998
INVENTOR(S) : Catherine CAUSSE et al.

It is certified that error appears in the above-identified patent and that said Letters Patent is hereby corrected as shown below:

On the title page, Item [54], and the top of column 1:
...SALICYCLIC... should read --SALICYLIC--

Signed and Sealed this

Fifth Day of May, 1998

Attest:

BRUCE LEHMAN

Attesting Officer        Commissioner of Patents and Trademarks